US012576057B2

(12) United States Patent
Lee et al.

(10) Patent No.: US 12,576,057 B2
(45) Date of Patent: Mar. 17, 2026

(54) ANTIBACTERIAL AND BIOFILM FORMATION-INHIBITING COMPOSITION CONTAINING MYRISTOLEIC ACID AS ACTIVE INGREDIENT

(71) Applicant: RESEARCH COOPERATION FOUNDATION OF YEUNGNAM UNIVERSITY, Gyeongsan-si (KR)

(72) Inventors: Jintae Lee, Daegu (KR); Jin-Hyung Lee, Daegu (KR); Jae-Gyu Park, Daegu (KR)

(73) Assignee: RESEARCH COOPERATION FOUNDATION OF YEUNGNAM UNIVERSITY, Gyeongsan-si (KR)

( * ) Notice: Subject to any disclaimer, the term of this patent is extended or adjusted under 35 U.S.C. 154(b) by 622 days.

(21) Appl. No.: 17/989,705

(22) Filed: Nov. 18, 2022

(65) Prior Publication Data

US 2023/0084268 A1 Mar. 16, 2023

Related U.S. Application Data

(63) Continuation of application No. PCT/KR2020/012797, filed on Sep. 22, 2020.

(30) Foreign Application Priority Data

May 20, 2020 (KR) ........................ 10-2020-0060372

(51) Int. Cl.
*A61K 31/201* (2006.01)
*A61P 17/10* (2006.01)
*A61P 31/04* (2006.01)

(52) U.S. Cl.
CPC ............ *A61K 31/201* (2013.01); *A61P 17/10* (2018.01); *A61P 31/04* (2018.01)

(58) Field of Classification Search
CPC ......... A61P 31/04; A61P 17/10; A61K 31/201
See application file for complete search history.

(56) References Cited

U.S. PATENT DOCUMENTS

2011/0034557 A1 2/2011 Jarrell et al.

FOREIGN PATENT DOCUMENTS

| KR | 10-0981523 | B1 | 9/2010 |
| KR | 10-2013-0128141 | A | 11/2013 |
| KR | 10-2018-0066103 | A | 6/2018 |
| KR | 10-0981523 | * | 9/2020 |
| WO | 2009/009885 | A1 | 1/2009 |

OTHER PUBLICATIONS

Jin-Hyung Lee et al., "Supercritical fluid extracts of Moringa oleifera and their unsaturated fatty acid components inhibit biofilm formation by *Staphylococcus aureus*", vol. 80, Oct. 2017, pp. 74-82.
Jin-Hyung Lee et al., "3-Indolylacetonitrile Decreases *Escherichia coli* O157:H7 Biofilm Formation and Pseudomonas aeruginosa Virulence", Environmental Microbiology, 2011, 13(1), pp. 62-73.
Chandran Sivasankar et al., "A combination of ellagic acid and tetracycline inhibits biofilm formation and the associated virulence of Propionibacterium acnes in vitro and in vivo", Biofouling, 2016, vol. 32, No. 4, 397-410.
Mel Rosenberg et al., "Adherence of bacteria to hydrocarbons: A simple method for measuring cell-surface hydrophobicity", FEMS Microbiology Letters, vol. 9, Issue 1, Sep. 1980, pp. 29-33.
Ana Luiza Mattos-Guaraldi et al., "Cell Surface Hydrophobicity of Sucrose Fermenting and Nonfermenting Corynebacterium diphtheriae Strains Evaluated by Different Methods", Current Microbiology, vol. 38, 1999, pp. 37-42.
Alejandro Beceiro et al., "Biological Cost of Different Mechanisms of Colistin Resistance and Their Impact on Virulence in Acinetobacter baumannii", Antimicrob Agents Chemother, Jan. 2014, 58(1): 518-526.
Satish Kumar Rajasekharan et al., "LED based real-time survival bioassays for nematode research", Scientific Reports, vol. 8, Article No. 11531 (2018).
Teruaki Nakatsuji et al., "Antimicrobial Property of Lauric Acid Against Propionibacterium acnes: Its Therapeutic Potential for Inflammatory Acne Vulgaris", J Invest Dermatol. Oct. 2009; 129(10): 2480-2488.
J W Costerton et al., "Bacterial Biofilms in Nature and Disease", Annual Review of Microbiology, vol. 41, 1987, Costerton, pp. 435-464.
Marion Nicol et al., "Unsaturated Fatty Acids Affect Quorum Sensing Communication System and Inhibit Motility and Biofilm Formation of Acinetobacter baumannii", Int. J. Mol. Sci. 2018, 19, 214; doi:10.3390/ijms19010214.
Hui Zhang et al., "Quantitative structure-activity relationships of antimicrobial fatty acids and derivatives against *Staphylococcus aureus*", Zhang et al. / J Zhejiang Univ-Sci B (Biomed & Biotechnol) 2012 13(2):83-93.

* cited by examiner

*Primary Examiner* — Marcos L Sznaidman
(74) *Attorney, Agent, or Firm* — Revolution IP, PLLC

(57) ABSTRACT

The present invention relates to an antibacterial and biofilm formation-inhibiting composition containing myristoleic acid as an active ingredient, wherein the myristoleic acid has been confirmed to exhibit an antibacterial effect against acne bacterium (*Cutibacterium acnes*) and *Staphylococcus aureus*, which cause skin inflammation and trouble, and to effectively inhibit the biofilms of *Cutibacterium acnes* and *Staphylococcus aureus*, at a very low concentration, and thus, the composition containing myristoleic acid as an active ingredient can be provided as an antibacterial agent and an anti-biofilm composition, and can be provided as a cosmetic composition for ameliorating skin inflammatory diseases.

3 Claims, 6 Drawing Sheets

[Fig. 1]
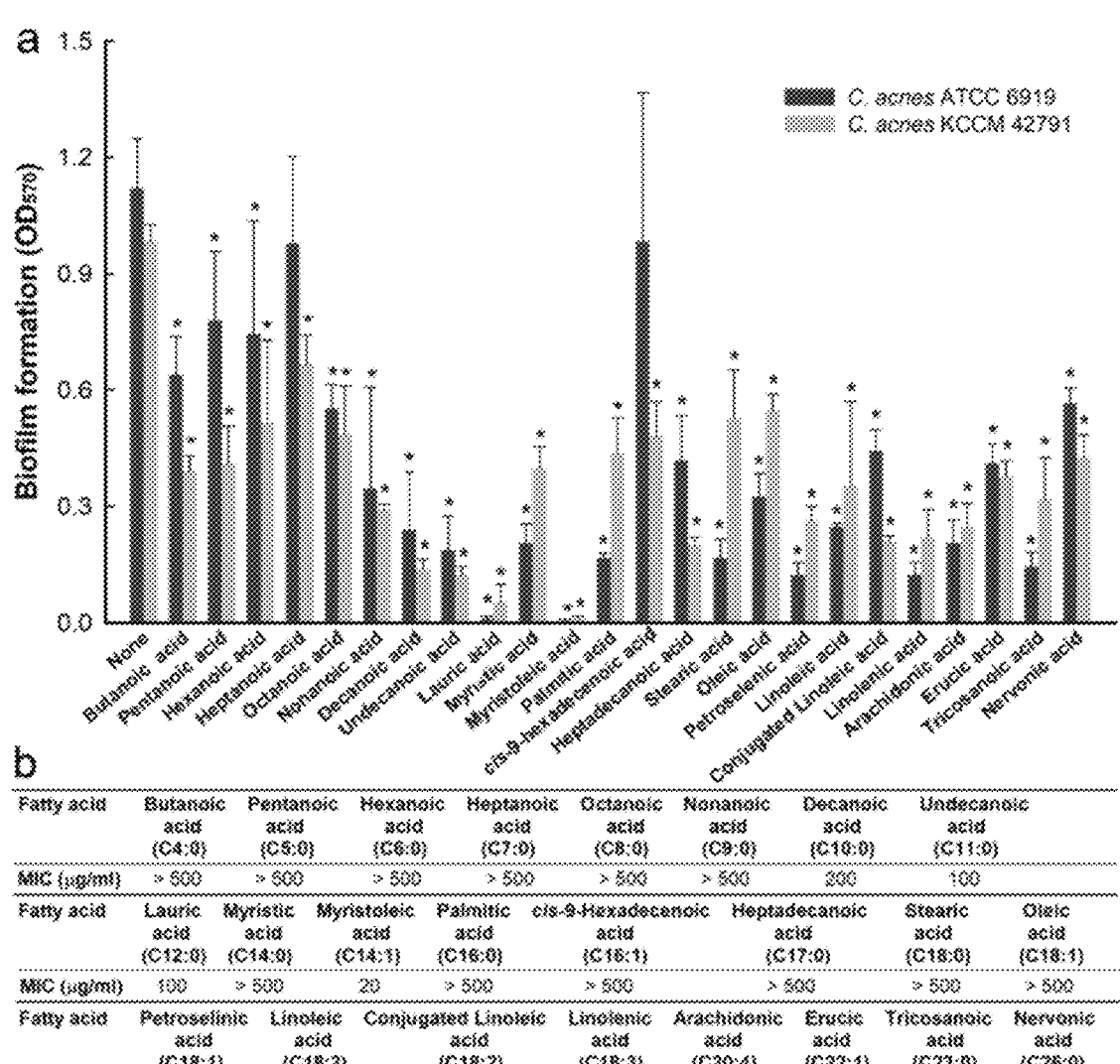

[Fig. 2]
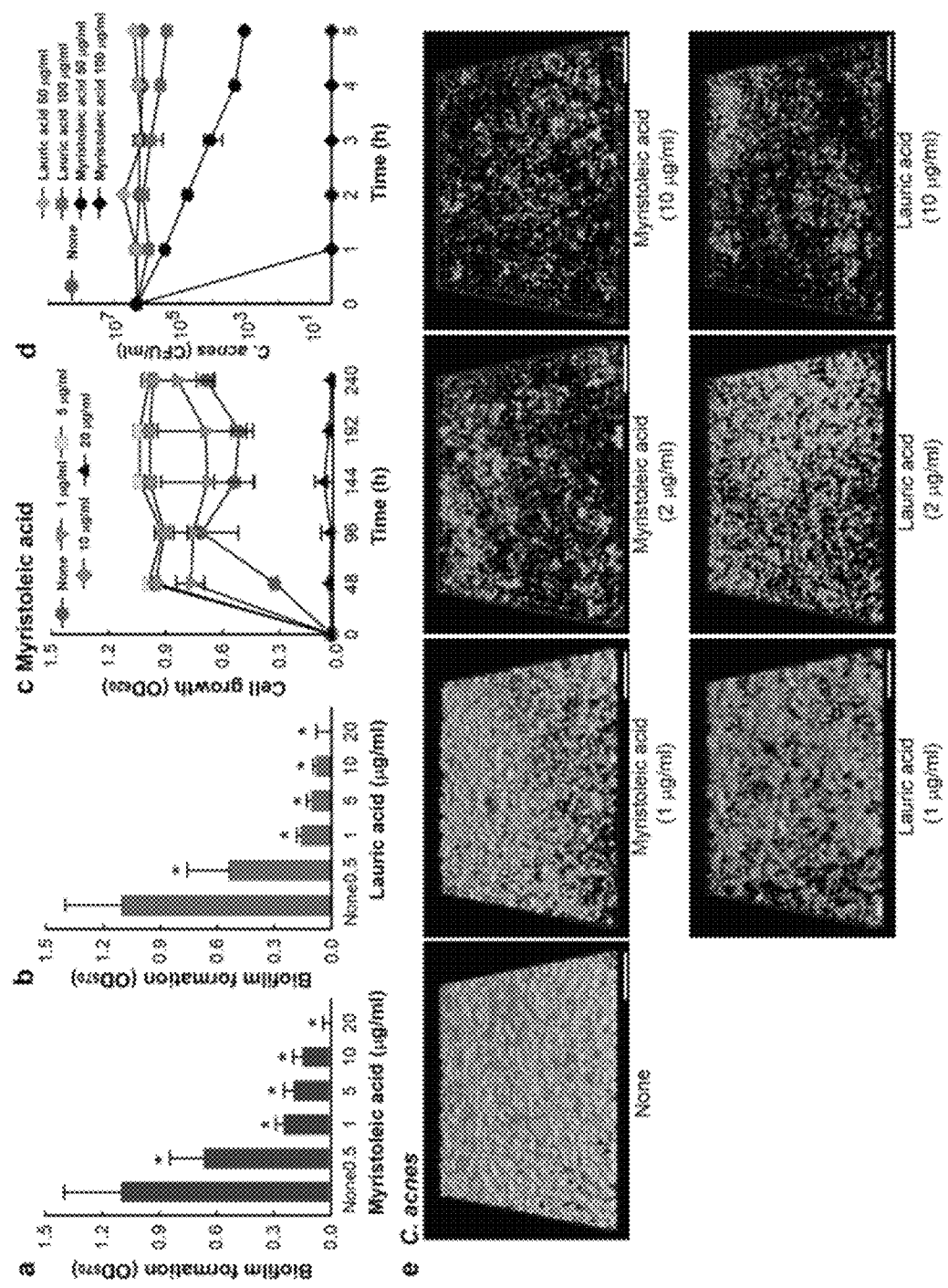

[Fig. 3]
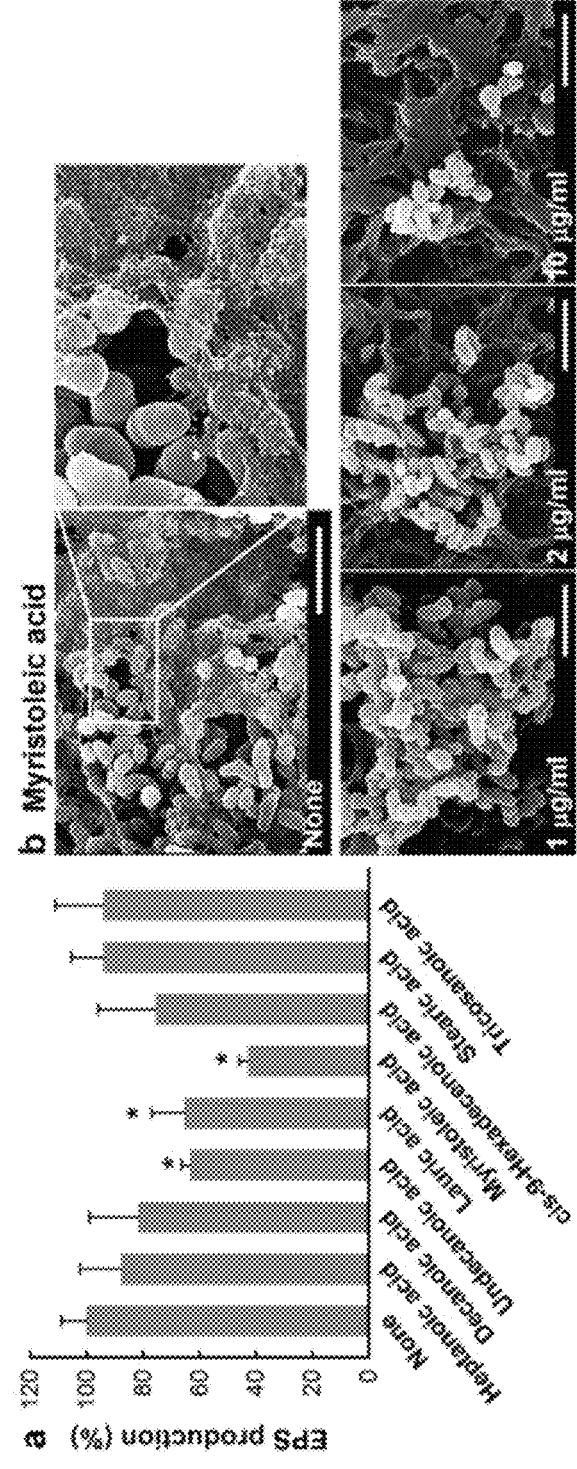

[Fig. 4]
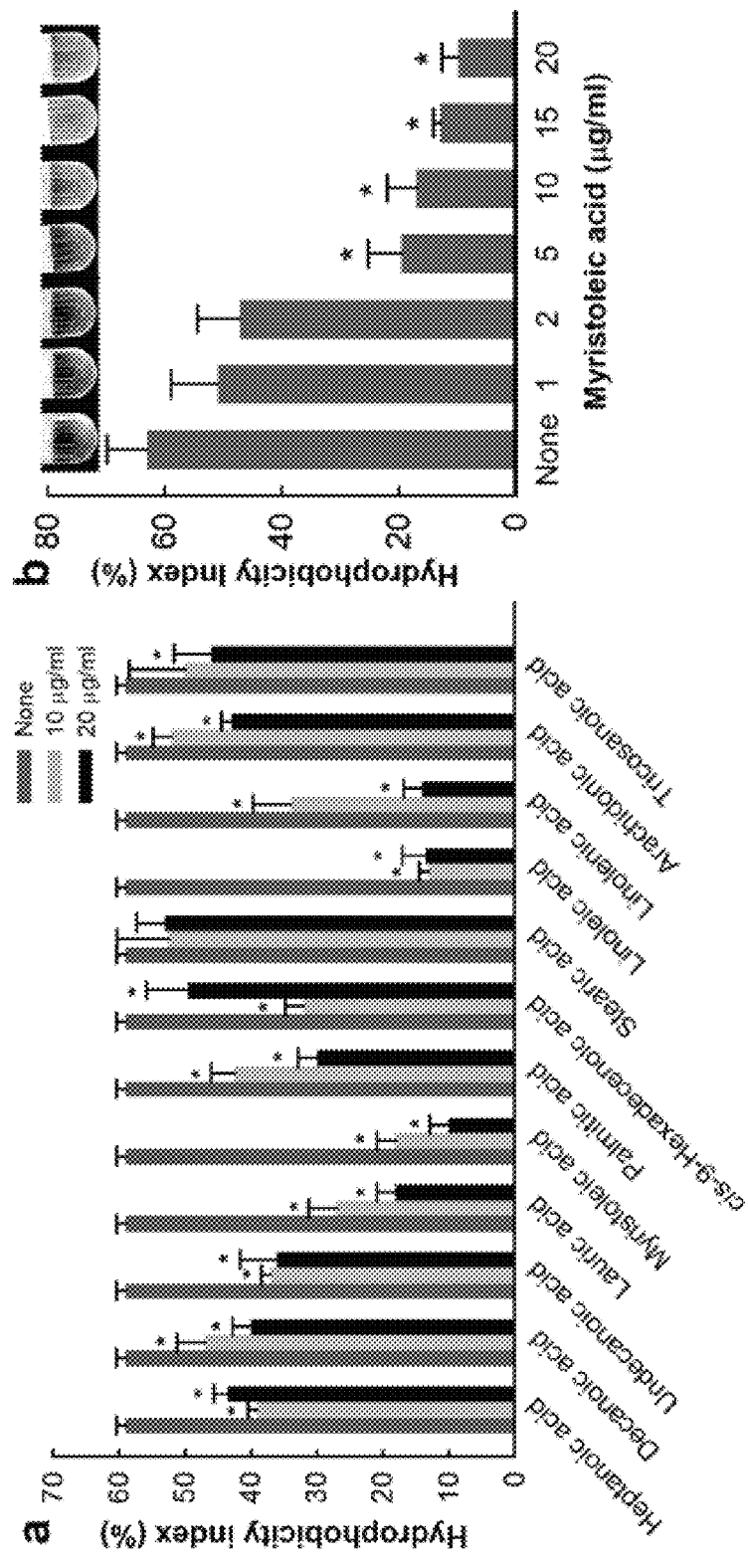

[Fig. 5]
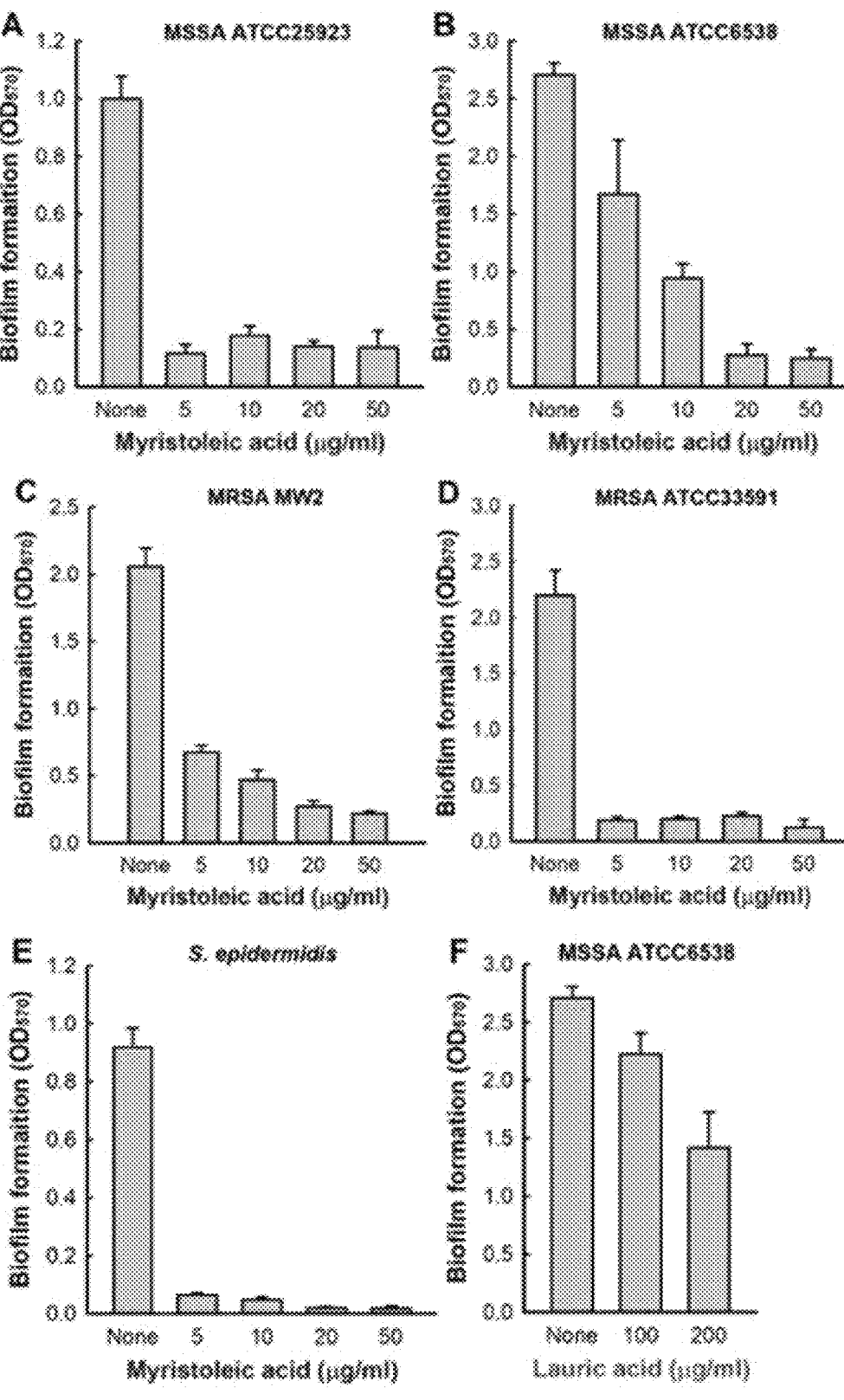

[Fig. 6]

ANTIBACTERIAL AND BIOFILM FORMATION-INHIBITING COMPOSITION CONTAINING MYRISTOLEIC ACID AS ACTIVE INGREDIENT

TECHNICAL FIELD

The present disclosure relates to an antibacterial and antibiofilm composition including myristoleic acid as an active ingredient.

BACKGROUND ART

Often present on a portion infected with bacteria is mucus which is a colony of bacteria surrounded by a polymer matrix. This mucinous bacterial complex formed by the bacteria is called a biofilm. The biofilm is a complex in which an outer layer which is a non-biological surface and a polymeric substrate composed of polysaccharides and polypeptides surrounds a bacterial colony which is a solid biological surface, helping bacteria communicate in the biofilm and defend against the external world. Thereby, the biofilm enables survival of bacteria under various environmental stresses including antibiotics and host immune systems.

Such the biofilm is frequently observed in bacterial infectious diseases. It may be formed in human organs, appear in the form of dental plaque, or exist in industrial equipment or medical implants. For this reason, biofilms have been the subject of interest by scholars studying periodontal disease, pneumonia accompanied with cystic fibrosis, and earache in the middle ear. The National Institutes of Health estimated in a 2002 report that up to 80% of bacterial colonies spread pathogens through formation of biofilms.

Antibiotics, which were effective against separately floating planktonic bacteria, also tend to lose efficacy when the bacteria form the biofilm. When bacteria form the biofilm, antibiotics barely penetrate the outer layer present on the biofilm, thereby inactivating the host immune system and increasing the resistance of bacteria to antibiotics by about 1,000 times. The cause of the increase in resistance to antibiotics due to formation of such the biofilm is not yet precisely known, but it may be explained by three factors listed below. The first factor is "ecological change of microorganisms". In a state in which the biofilm is formed, the binding force among bacteria becomes strong, making the bacterial colony hardly spread so as to cause deterioration in the bacterial growth. This weakens dependence on exchange with the surrounding environment, slows down metabolism, and consequently lowers sensitivity to antibiotics.

The second factor is the physical properties of the "outer layer composed of mucopolysaccharides". The mucopolysaccharides forming the outer layer have electrical properties and tend to bind with antibiotics, and such the binding with antibiotics prevents the spread of antibiotics. In other words, antibiotics are not properly delivered to each bacterium, barely deriving efficacy of the antibiotics.

The third factor is the "production of inhibitors", which is a presumption related to the general mechanism of antibiotic resistance acquisition. The substances best known as inhibitors for the efficacy of antibiotics may be β-lactamases produced by *Pseudomonas*. Once the biofilm is formed, even non-resistant bacteria present in the biofilm acquire resistance factor-related genes from neighboring resistant bacteria through horizontal gene transfer, thereby showing tendency to become resistant. In other words, when the biofilm is formed at the infected site, it may be considered to be in an antibiotic-resistant state.

For these reasons, when the biofilm is formed, antibiotics that have been widely used to treat infections hardly take action, such that the therapeutic effect of antibiotics is lessened so as to enter a chronic bacterial infection state. In this case, as described above, the sensitivity of bacteria to antibiotics is lowered, so even the use of antibiotics shows little effect, and an action of simply overprescribing antibiotics to overcome the situation will only increase the antibiotic resistance of bacteria. That is, it means that treatment simply with antibiotics would no longer an effective treatment for bacterial infection accompanied with biofilm formation. In particular, infection by bacteria forming the biofilm is often caused by multi-drug resistant bacteria that are resistant to various antibiotics, worsening the problem.

Therefore, in order to solve the above issue, there is a need to develop a therapeutic agent capable of destroying the biofilm or the outer layer present on the biofilm.

DISCLOSURE OF THE INVENTION

Technical Goals

In order to inhibit a biofilm of acne bacterium (*Cutibacterium acnes*) and *Staphylococcus aureus*, which cause dermatitis diseases and skin troubles, and improve to germicidal effects, the present disclosure provides myristoleic acid as an antibacterial and antibiofilm composition.

Technical Solutions

The present disclosure provides a biofilm formation-inhibiting composition including myristoleic acid as an active ingredient.

In addition, the present disclosure provides an antibacterial composition including myristoleic acid as an active ingredient.

In addition, the present disclosure provides a cosmetic composition for preventing or ameliorating dermatitis diseases or skin troubles, including myristoleic acid as an active ingredient.

Advantageous Effects

According to the present disclosure, it was found that myristoleic acid exhibits an antibacterial effect against acne bacterium (*Cutibacterium acnes*) and *Staphylococcus aureus*, which cause skin inflammation and trouble, and effectively inhibits biofilms of *C. acnes* and *S. aureus* at a very low concentration, such that a composition including the myristoleic acid as an active ingredient may be provided as an antibacterial agent and an antibiofilm composition and also as a cosmetic composition for ameliorating skin inflammatory diseases.

BRIEF DESCRIPTION OF DRAWINGS

FIG. 1 shows results of identifying the effect of various fatty acids on biofilm formation and cell growth of *C. acnes*, wherein (A) is a result of identifying the anti-biofilm activity of fatty acids for *C. acnes* strains after culturing two types of *C. acnes* strains in RCM medium for 96 hours on a 96-well plate with all fatty acids treated at a concentration of 20 μg/ml (*, $P < 0.05$ vs. untreated control), and (B) is a result showing MIC of each fatty acid for *C. acnes* ATCC 6919.

FIG. 2 shows results of identifying the antibiofilm and antimicrobial activity of myristoleic acid against *C. acnes*, wherein (A) is a result of quantifying biofilm formation of *C. acnes* ATCC 6919 after 96 hours of culture in the presence of myristoleic acid, (B) is a result of quantifying biofilm formation of *C. acnes* ATCC 6919 after 96 hours of culture in the presence of lauric acid, with the error bars representing the standard deviation (*, P<0.05 vs. untreated control), (C) is a result of identifying the planktonic cell growth of *C. acnes* ATCC 6919 treated with myristoleic acid, (D) is a result of identifying rapid killing effect of *C. acnes* ATCC 6919 by myristoleic acid and lauric acid, and (E) is fluorescence micrographic images for inhibition of *C. acnes* ATCC 6919 biofilm formation by myristoleic acid and lauric acid.

FIG. 3 shows results of identifying the effect of myristoleic acid on exopolymeric substances (EPS), wherein (A) is a result of quantifying *C. acnes* ATCC 6919 in which EPS was produced after 96 hours of culture by treatment with 0 and 10 μg/ml of fatty acids, and (B) is results of identifying a biofilm of *C. acnes* treated or untreated with myristoleic acid (1, 2 and 10 μg/ml) using SEM.

FIG. 4 shows results of identifying the effect of fatty acids on the hydrophobicity of *C. acnes*, wherein (A) is a result of identifying the cell surface hydrophobicity of *C. acnes* ATCC 6919 after 96 hours of culture with 0, 10, and 20 μg/ml of fatty acids, and (B) is a result of identifying the dose-dependent effect of myristoleic acid on the hydrophobicity of *C. acnes*.

FIG. 5 shows results of identifying the biofilm inhibitory activity of myristoleic acid against *S. aureus* strains and *S. epidermidis* strains, wherein (A) is a result of identifying biofilm formation of *S. aureus* ATCC 6538, (B) is a result of identifying biofilm formation of *S. aureus* ATCC 25923, (C) is a result of identifying biofilm formation of MRSA MW2, (D) is a result of identifying biofilm formation of MRSA ATCC 33591, obtained by culture on a 96-well plate in the presence of myristoleic acid or lauric acid, and (E) is a result of identifying biofilm formation of *S. epidermidis* ATCC 14990, quantified after 24 hours of culture in LB medium (*, P<0.05 vs. untreated control).

FIG. 6 shows results of identifying the effect of myristoleic acid on *C. elegans* infected with *C. acnes* and toxicity thereof, wherein (A) is a result of identifying the survival of nematode after inoculation with *C. acnes* ATCC 6919 in the presence or absence of myristoleic acid, and (B) shows a result of identifying the toxicity of myristoleic acid by treating uninfected *C. elegans* with myristoleic acid for 5 days, wherein None indicates untreated cells (*, P<0.05 vs. untreated control).

BEST MODE FOR CARRYING OUT THE INVENTION

Hereinafter, the present disclosure will be described in detail.

During the research for an antibacterial and antibiofilm composition using various fatty acids, the present inventors completed the present disclosure by discovering that, unlike other fatty acids, myristoleic acid effectively inhibits biofilm formation by acne bacteria *Cutibacterium acnes* and *Staphylococcus aureus* at a very low concentration.

The present disclosure may provide a biofilm formation-inhibiting composition including myristoleic acid as an active ingredient.

The myristoleic acid may inhibit biofilm formation of one or more strains selected from the group consisting of *Cutibacterium acnes* and *Staphylococcus* strains.

The acne bacteria may be selected from the group consisting of *Cutibacterium acnes*(*C. acnes*) strain KCCM 41747 (ATCC 6919) and *Cutibacterium acnes* strain KCCM 42791.

The *Staphylococcus* strain may be selected from the group consisting of methicillin-sensitive *Staphylococcus aureus* strain ATCC 25923, methicillin-sensitive *Staphylococcus aureus* strain ATCC 6538, methicillin-resistant *Staphylococcus aureus* strain MW2, methicillin-resistant *Staphylococcus aureus* strain ATCC 33591, and *Staphylococcus epidermidis* (*S. epidermidis*) strain.

The present disclosure may provide an antibacterial composition including myristoleic acid as an active ingredient.

The myristoleic acid may kill one or more strains selected from the group consisting of *Cutibacterium acnes* and *Staphylococcus* strains.

The present disclosure may provide a cosmetic composition for preventing or ameliorating a dermatitis disease or skin trouble, including myristoleic acid as an active ingredient.

The dermatitis disease or skin trouble may be caused by acne bacteria (*Cutibacterium acnes*), *Staphylococcus* strains, or a biofilm thereof.

The dermatitis diseases may be selected from the group consisting of comedonal acne, acne papular, pustular acne, crystalline acne, cystic acne, acne vulgaris, acne fulminans, acne conglobata, acne keloidalis, psoriasis, atopic dermatitis, seborrheic dermatitis, contact dermatitis, nummular eczema, and general dermatitis.

The cosmetic composition may include, in addition to myristoleic acid as the active ingredient, a stabilizer, a solubilizer, a conventional supplement such as vitamins, pigments, and fragrances, and a carrier.

The cosmetic composition may be prepared in any formulation conventionally prepared in the art, for example, a solution, suspension, emulsion, paste, gel, cream, lotion, powder, oil, powder foundation, emulsion foundation, wax foundation, and spray, but is not limited thereto. More specifically, it may be prepared in the form of a sun screen, softening lotion, astringent lotion, nourishing lotion, nourishing cream, massage cream, essence, eye cream, pack, spray, or powder.

When the formulation is a paste, cream or gel, animal oil, vegetable oil, wax, paraffin, starch, tracanth, cellulose derivative, polyethylene glycol, silicone, bentonite, silica, talc, or zinc oxide may be used as a carrier component.

When the formulation is the powder or spray, lactose, talc, silica, aluminum hydroxide, calcium silicate or polyamide powder may be used as the carrier component, and in particular, in the case of the spray, it may additionally include a booster such as chlorofluorohydrocarbon, propane/butane, or dimethyl ether.

When the formulation is the solution or emulsion, a solvent, solubilizer, or emulsifier may be used as the carrier component, including, for example, water, ethanol, isopropanol, ethyl carbonate, ethyl acetate, benzyl alcohol, benzyl benzoate, propylene glycol, 1,3-butylglycol oil, glycerol fatty ester, polyethylene glycol, or fatty acid ester of sorbitan.

When the formulation is the suspension, a liquid diluent such as water, ethanol or propylene glycol, a suspending agent such as ethoxylated isostearyl alcohol, polyoxyethylene sorbitol ester, and polyoxyethylene sorbitan ester, microcrystalline cellulose, aluminum metahydroxide, bentonite, agar, or tracanth may be used as the carrier component.

MODES FOR CARRYING OUT THE INVENTION

Hereinafter, to help the understanding of the present disclosure, example embodiments will be described in detail. However, the following example embodiments are merely illustrative of the contents of the present disclosure, and the scope of the present disclosure is not limited to the following examples. The example embodiments of the present disclosure are provided to more completely explain the present disclosure to those of ordinary skill in the art.

Experimental Example

The following experimental examples are intended to provide experimental examples commonly applied to each example embodiment according to the present disclosure.

1. Strains, Compounds and Culture Conditions

*Cutibacterium acnes* strain KCCM 41747 (ATCC 6919, isolated from human facial acne) and *C. acnes* strain KCCM 42791 (isolated from dental plaque) were used. The strain was obtained from Korean Culture Center for Microorganisms (KCCM, Seoul, Korea) and cultured on Reinforced *Clostridium* Media (RCM) agar plates to prepare colonies, and all the additional experiments were performed using liquid RCM at 37° C. under anaerobic conditions, wherein BD GasPak™ EZ Gas Generating Anaerobic Pouch Systems (Fisher Scientific, Pittsburgh, USA) was used for maintenance.

A total of 24 fatty acids were purchased from Sigma Aldrich (St. Louis, USA) or TCI Co. (Tokyo, Japan), including butanoic acid, pentanoic acid, hexanoic acid, heptanoic acid, octanoic acid, nonanoic acid, decanoic acid, undecanoic acid, lauric acid, myristic acid, myristoleic acid, palmitic acid, cis-9 hexadecenoic acid, heptadecanoic acid, stearic acid, oleic acid, petroselinic acid, linoleic acid, linolenic acid, conjugated linoleic acid, arachidonic acid, erucic acid, tricosanoic acid, and nervonic acid.

Dimethyl sulfoxide (DMSO) was used as a solvent for dissolving all fatty acids except butyric acid, and DMSO (0.1% v/v) was used as a negative control. DMSO contained in an amount less than or equal to 0.1% did not have any effect on bacterial growth or biofilm formation.

2. Measurement of Planktonic Cell Growth and MIC Identification

In order to identify the effect of fatty acids on the planktonic growth of *C. acnes*, a culture cultured for 96 hours in a 96-well plate was re-transplanted after undergoing dilution in a ratio of 1:50 and then treated with fatty acids of different concentrations.

Plates were cultured under anaerobic condition at 37° C. and maintained using an anaerobic pouch (Fisher Scientific, Pittsburgh, USA). After 96 hours of culture, cell turbidity was checked at 600 nm using Optizen 2120UV spectrophotometer (Mecasys Co. Ltd., Daejeon, Korea).

3. Crystal Violet Film Assay

Crystal violet assay was performed by the previously reported method (Lee et al., 2017b) to quantify biofilm formation.

Briefly, *C. acnes*, which showed an initial OD value of OD 2.3 (CFU ~$10^8$) cells/ml at 600 nm and underwent 96 hours of culture, was diluted in a ratio of 1:50 with sterile RCM medium and then spread on the 96-well plate in the presence or absence of fatty acids, followed by culture at 37° C. under anaerobic conditions for 96 hours.

To quantify the biofilm, planktonic growth was eliminated, the plate was washed three times with distilled water, and the biofilm attached to the well was stained with 0.1% crystal violet for 20 minutes. Thereafter, the plate was washed three times with sterile distilled water, and crystal violet was extracted using 95% ethanol, absorbance was measured at 570 nm using Multiskan EX microplate reader (Thermo Fisher Scientific, Waltham, MA), and the result was shown as an average value of at least 12 replicate wells.

Percentage for inhibition rate represents relative biofilm formation (100×biofilm formation with chemical/biofilm formation of untreated control).

4. Analysis of Rapid Killing of Acne Bacteria Using Fatty Acids

To determine the killing time by fatty acids, a time-kill experiment was performed. Briefly, cultures of *C. acnes* ATCC 6919 grown in RCM broth (BD Difco™, Fisher Scientific, Pittsburgh, USA) at 37° C. under anaerobic conditions for 96 hours were diluted in a ratio of 1:50 with fresh RCM medium.

The samples were treated with myristoleic acid (50 and 100 μg/ml) or lauric acid (50 and 100 μg/ml) and cultured at 37° C. under anaerobic conditions while stirring.

At each time point, aliquots of treated cells were collected, and after performing appropriate dilutions, cells were smeared on RCM agar plates and incubated at 37° C. for 96 hours, followed by enumeration of CFUs, wherein each experiment was repeated.

5. Scanning Electron Microscopy

Production of extracellular polymeric substance (EPS) was detected by electron microscopy (SEM) by the previously reported method (Lee et al., 2011).

Briefly, *C. acnes* cells were inoculated in 96-well plates under conditions with or without fatty acids, and a nylon filter (0.4×0.4 mm square) was added to each well. Biofilms were grown on the nylon filters by culturing together for 96 hours without stirring under anaerobic conditions at 37° C.

Then, the biofilm cells on the piece of nylon filter were immobilized with 2.5% glutaraldehyde and 2% formaldehyde for 24 hours and sequentially immobilized with osmium tetroxide, followed by dehydration with ethanol series (50, 70, 80, 90, 95 and 100%) and isoamyl acetate.

After critical point drying, the cells on the filter were stopper-coated with to palladium/gold, and observed under an S-4100 scanning electron microscope (Hitachi, Tokyo, Japan) at a magnification of ×1000 to ×10,000 using an acceleration voltage of 15 kV.

6. Quantification of Extracellular Polymeric Substance (EPS)

For EPS quantification, *C. acnes* treated with control and myristoleic acid was cultured at 37° C. for 96 hours. After culture, the culture was centrifuged at 8,228×g for 10 minutes, and the supernatant was separated.

The cell pellet was washed with sterile PBS to remove the culture supernatant which is free of residual cells. 15 ml of an isotonic solution (10 mM Tris/HCl, pH 8.0, 10 mM EDTA, 2.5% NaCl) was added to the cell pellet, and the mixed wells were culture at 4° C. overnight.

After overnight culture, the cell suspension was shaken to be mixed for 5 minutes, followed by centrifugation at 8,228×g for 10 minutes. The supernatant containing EPS bound with the cells was separated from the cells. Cold ethanol was added to the supernatant in a ratio of 1:3 and left at −20° C. overnight.

After collecting the precipitated EPS by centrifugation at 4° C., 18,514×g for 30 minutes, the pellet was washed with 70% ethanol and dried. The dried EPS was weighed, and inhibition of EPS production by fatty acids was calculated by the following formula (Sivasankar et al., 2016).

([Control wt−Treated wt/Control wt]×100)

7. Hydrophobicity Analysis: Microbial Adherence to Hydrocarbon (MATH)

MATH analysis (Rosenberg et al., 1980) was performed to identify the effect of fatty acids on the attachability of *C. acnes* to hydrocarbons (toluene) and the cell surface hydrophobicity of *C. acnes*.

*C. acnes* were grown without fatty acids for 96 hours under anaerobic conditions at 37° C.

After incubation, a cell suspension of a myristoleic acid-free control and a myristoleic acid-treated culture (5, 10, 15, or 20 μg/ml) was prepared using sterile PBS. The OD values of all treated and untreated cultures were adjusted to OD 0.5±0.05, and an equal volume of toluene was added to 3 ml of the cell suspension, followed by stirring for 60 seconds.

After stirring, incubation of an aqueous solution was performed overnight at room temperature to completely remove the trace solvent. $OD_{600}$ in the aqueous solution was observed and cell surface hydrophobicity (CSH) was evaluated by hydrophobicity index (HI) using the following formula.

$$(HI=[1-(OD_{600} \text{ after vortexing}/OD_{600} \text{ before vortexing})]\times100) \text{ (Mattos-Guaraldi et al., 1999).}$$

8. Identification of Anti-Viral Effect and Cytotoxicity of Myristoleic Acid in Nematode Model

*C. elegans* killing assay was performed with a slight modification of the previously reported method (Beceiro et al., 2014). Briefly, assays were performed in 96-well plates. Young adult nematodes (20-30) [fer-15(b26);fem-1 (hc17)] were transferred to each well contained in an M9 solution. The untreated control and fatty acid-treated *C. acnes* cells were each added to separate wells containing 20 to 30 nematodes and incubated at 25° C.

Nematodes solely exposed to *E. coli* OP50 at CFU of 1×10⁶ cells/ml were used as a control.

Viability was identified by exposing to LED or UV LED light for 10 to 30 seconds using the iRiS™ Digital Cell Imaging System (Logos BioSystems, South Korea) by the previously reported method (Rajasekharan et al., 2018). The experiments were repeated three times.

The toxicity of myristoleic acid was identified in *C. acnes*. *C. acnes* was treated with myristoleic acid with various doses, and survival was checked every day for 5 consecutive days.

<Example 1> Identification of Antibacterial and Anti-Biofilm Activity of Various Fatty Acids Against *C. acnes*

To identify a novel anti-biofilm agent, the minimal antibacterial effect of 24 fatty acids (14 saturated fatty acids and 10 unsaturated fatty acids) was screened at a concentration of 20 ng/ml in a 96-well plate.

As a result of identifying formation of *C. acnes* biofilms in the presence of fatty acids, as shown in FIG. 1A, most fatty acids showed very different inhibitory efficiencies in the biofilm formation for two types of *C. acnes* strains (ATCC 6919 and KCCM 42791).

In particular, 17 fatty acids (nonanoic acid, decanoic acid, undecanoic acid, lauric acid, myristic acid, myristoleic acid, palmitic acid, heptadecanoic acid, stearic acid, oleic acid, petrocelic acid, linoleic acid, linolenic acid, conjugated linoleic acid, arachidonic acid, erucic acid, and trichoic acid) inhibited formation of *C. acnes* biofilms by more than 60% at a concentration of 20 μg/ml, whereas three fatty acids (valeric acid, heptanoic acid, and cis-9-hexadecenoic acid) caused very subtle changes in biofilm formation for the *C. acnes* ATCC to 691 strain. Fatty acids that increased biofilm formation of *C. acnes* under the same conditions were not observed.

The anti-biofilm effect of most fatty acids was similarly identified in another *C. acnes* strain KCCM 42791 isolated from plaque.

In particular, it was found that lauric acid and myristoleic acid at a concentration of 20 μg/ml showed more than 95% of *C. acnes* biofilm formation inhibitory effect.

According to the previous report, it was found that lauric acid showed antibacterial activity against *C. acnes* with MIC of 60 μg/ml after 72 hours (Nakatsuji et al., 2009).

Accordingly, the effect of myristoleic acid and lauric acid as a control was identified using the *C. acnes* ATCC 6919 strain which is widely used in research for *C. acnes* biofilms.

The MIC of fatty acids was determined with reference to FIG. 1B.

While the MIC of most FAs is 500 μg/ml or more, that of four medium-chain fatty acids (MCFAs) such as decanoic acid, undecanoic acid, lauric acid, and myristoleic acid showed a concentration range of 20 to 200 μg/ml after 96 hours of culture.

In particular, myristoleic acid and lauric acid exhibited a very significant biofilm formation inhibitory effect by more than 98%, and the MICs of myristoleic acid and lauric acid were found to be 20 μg/ml and 100 μg/ml, respectively.

The antibacterial activity of lauric acid and decanoic acid has already been identified in the previous report, which was very similar to the result of FIG. 1B. However, the *C. acnes* biofilm inhibitory activity by fatty acids below the inhibitory level is not mentioned at all.

<Example 2> Identification of the Inhibitory Effect of Myristoleic Acid and Lauric Acid on *C. acnes* Biofilm Formation In order to observe a more detailed biofilm test result, the inhibitory effect on *C. acnes* biofilm formation was identified in accordance with doses of myristoleic acid and lauric acid in a 96-well polystyrene plate.

As a result, as shown in FIGS. 2A and 2B, myristoleic acid and lauric acid exhibited an inhibitory effect on biofilm formation of 80% or higher at 1 μg/ml, and it was found that the MIC of myristoleic acid (20 μg/ml) was 5 times lower than that of lauric acid (100 μg/ml), a well-known anti-acne agent. In addition, referring to FIG. 2C, myristoleic acid did not reduce planktonic cell growth even when increased to 10 μg/ml.

When applied to anti-acne treatment, one of the properties to be considered is its fast action.

Accordingly, the time required for cell death of *C. acnes* in the presence of myristoleic acid and lauric acid was determined.

As a result, as shown in FIG. 2D, myristoleic acid killed most of *C. acnes* cells (99.999% or more) in 1 hour at a concentration of 100 μg/ml, whereas lauric acid did not effectively kill *C. acnes* cells at the same concentration.

From the above results, it was found that myristoleic acids at a high concentration may induce the immediate killing effect, while that in the minimum inhibitory concentration (<10 µg/ml) significantly inhibited *C. acnes* biofilm formation.

<Example 3> Identification of the Effect of Myristoleic Acid and Lauric Acid on Reduction of Extracellular Polymeric Substance (EPS) Production Production of extracellular polymer substances (EPSs) is a major feature of biofilm formation, binding planktonic cells to help protect themselves from the harsh external environment (Costerton et al., 1987).

Accordingly, EPS production was observed in the presence of several fatty acids, and the *C. acnes* biofilm formation inhibitory effect of the fatty acids was identified.

As a result, as shown in FIG. 3B, a significant reduction in EPS production was observed at a concentration of 10 µg/ml of undecanoic acid, lauric acid, and myristoleic acid, while, as shown in FIG. 3A, no significant changes were observed with other anti-biofilm fatty acids (decanoic acid, stearic acid, and trichoic acid) and less effective fatty acids (heptanoic acid and cis-9-hexadecenoic acid). SEM analysis also showed reduction in EPS production in the experimental group treated with myristoleic acid at a concentration of 10 µg/ml as shown in FIG. 3B.

From the above results, it was found that the anti-biofilm activity of fatty acids against *C. acnes* was due to inhibition of EPS production.

<Example 4> Identification of the Effect of Fatty Acids on Hydrophobicity of *C. acnes* Cells Cell surface hydrophobicity plays a crucial role in initial attachment or detachment to the surface.

In general, many hydrophobic cells tend to adhere more to hydrophobic surfaces such as polystyrene, polypropylene, silicon, and Teflon while hydrophilic cells may adhere to hydrophilic surfaces.

Accordingly, cell surface hydrophobicity was identified in the presence of 12 fatty acids which are active or less active in biofilm inhibition.

If the hydrophobicity index of bacteria is greater than (>50%) in the absence of fatty acids, it was found that the bacteria were considered hydrophobic, and *C. acnes* was less hydrophobic (60% hydrophobicity index).

Referring to FIG. 4A, 10 active anti-biofilm fatty acids reduced hydrophobicity of *C. acnes* and made the cells hydrophilic (hydrophobicity index <50%). This is an outcome derived by the fatty acids inhibiting biofilm formation as shown in FIG. 1A.

From the above results, it was found that the hydrophobicity reduction rate by fatty acids was related to their anti-biofilm effect.

Active lauric acid, myristoleic acid, and linoleic acid reduced cell hydrophobicity the most, whereas heptadecanoic acid, cis-9-hexadecenoic acid, stearic acid, and trichoic acid which are less active showed a little change in hydrophobicity.

More specifically, referring to FIG. 4B, myristoleic acid made *C. acnes* cells hydrophilic (>20%) at a concentration of 10 ng/ml and showed a clear-cut decrease in hydrophobicity in a dose-dependent manner.

From the above results, it may be suggested that the decrease in cell surface hydrophobicity by fatty acids is one of the plausible causes of the anti-biofilm activity of fatty acids.

<Example 5> Identification of Antibacterial and Antibiotic Film Activity of Myristoleic Acid Against *Staphylococcus* Strains The antibacterial and anti-biofilm activity of myristoleic acid against five *Staphylococcus aureus* strains was identified, including two methicillin-sensitive *S. aureus* strains (MSSA; ATCC 25923 and ATCC 6538), two methicillin-resistant *S. aureus* strains (MRSA, MW2, and ATCC 33591), and *S. epidermidis* strains.

As a result, as shown in FIG. 5, myristoleic acid exhibited strong anti-biofilm activity against 5 *Staphylococcus aureus* strains. Myristoleic acid at a concentration of 50 µg/ml showed the biofilm formation inhibitory effect of more than 90% for all 5 strains, whereas lauric acid showed weak anti-biofilm activity against *S. aureus* ATCC 6538. In addition, the MIC of myristoleic acid was found to be 150 µg/ml.

Accordingly, it was found that the anti-biofilm activity of myristoleic acid was due to partial antibacterial activity. In addition, since bacteria often form multi-species biofilms with other bacteria, myristoleic acid may be used to inhibit multi-species biofilms of *C. acnes* and *S. aureus*.

<Example 6> Identification of the Effect of Myristoleic Acid and Lauric Acid on Detoxification of *C. acnes* in Nematode Model The nematode *C. elegans* has been used as an alternative analysis method to determine the toxicity of various pathogenic bacteria, and *C. acnes* has been reported to exhibit toxicity to the nematode *C. elegans* (Sivasankar et al., 2016), such that a *C. elegans* killing assay was carried out to determine whether fatty acids may have an effect on *C. acnes* toxicity in nematodes.

Figure 6:
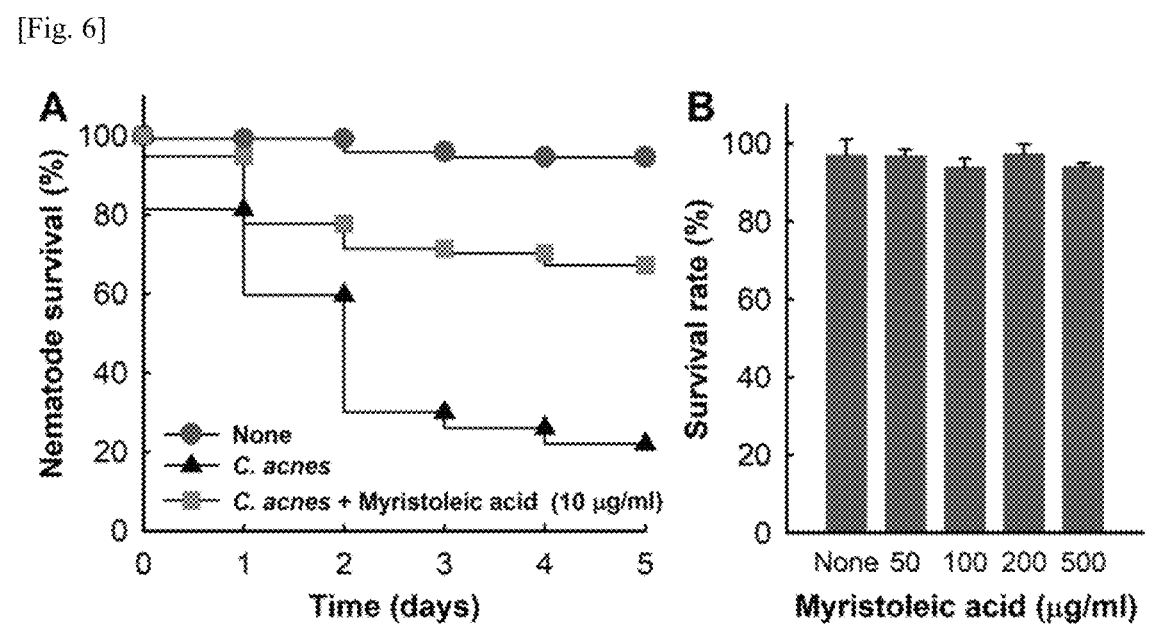

As a result, as shown in FIG. 6A, when myristoleic acid was treated at a concentration of 10 µg/ml, it was found that the survival of nematodes was increased even in the presence of *C. acnes* infection. More specifically, only 20% of *C. elegans* infected with C. acnes for 4 days survived, whereas 70% of *C. elegans* infected with C. acnes in the presence of myristoleic acid survived.

In addition, in order to identify the chemical toxicity of myristoleic acid, uninfected nematodes were exposed to different concentrations of myristoleic acid. As a result, as shown in FIG. 6B, myristoleic acid that was increased to 500 µg/ml for 5 days did not show toxicity to *C. elegans*.

From the above results, it was found that myristoleic acid effectively reduced the toxicity of *C. acnes* and increased survival without toxicity on infected nematodes.

As described above, a specific part of the content of the present disclosure is described in detail, for those of ordinary skill in the art, it is clear that the specific description is only a preferred embodiment, and the scope of the present disclosure is not limited thereby. Accordingly, the substantial scope of the present disclosure may be defined by the appended claims and their equivalents.

The invention claimed is:

1. A method of treating a dermatitis disease, comprising: administering a biofilm formation-inhibiting composition comprising myristoleic acid as an active ingredient to a subject, wherein the myristoleic acid inhibits biofilm formation of one or more strains selected from the group consisting of Cutibacterium *acnes* and *Staphylococcus* strains wherein the dermatitis disease is characterized by a biofilm formed by bacteria, and, wherein the dermatitis disease is selected from the group consisting of comedonal acne, acne papular, pustular acne, crystalline acne, cystic acne, acne vulgaris, acne fulminans, acne conglobata, acne keloidalis, psoriasis, atopic dermatitis, seborrheic dermatitis, contact dermatitis, nummular eczema, and general dermatitis.

2. The method of claim 1, wherein the *Cutibacterium acnes* is selected from the group consisting of *Cutibacterium acnes* (*C. acnes*) strain KCCM 41747 (ATCC 6919) and *C. acnes* strain KCCM 42791.

3. The method of claim 1, wherein the *Staphylococcus* strain is selected from the group consisting of methicillin-sensitive *Staphylococcus aureus* strain ATCC 25923, methicillin-sensitive *Staphylococcus aureus* strain ATCC 6538, methicillin-resistant *Staphylococcus aureus* strain MW2, methicillin-resistant *Staphylococcus aureus* strain ATCC 33591, and *Staphylococcus epidermidis* (*S. epidermidis*) strain.

\* \* \* \* \*